United States Patent [19]  [11]  4,384,125
Goettsch et al.  [45]  May 17, 1983

[54] PROCESS FOR THE PURIFICATION OF 2-PYRROLIDONE

[75] Inventors: Reijer Goettsch, Beek; Arnold G. M. Jetten, Ulestraten, both of Netherlands

[73] Assignee: Stamicarbon, B.V., Geleen, Netherlands

[21] Appl. No.: 271,933

[22] Filed: Jun. 9, 1981

[30] Foreign Application Priority Data

Jun. 10, 1980 [NL] Netherlands ............... 8003365

[51] Int. Cl.³ .................................. C07D 207/267
[52] U.S. Cl. .................................. 548/555; 548/543
[58] Field of Search .................... 260/326.5 FN

[56] References Cited

U.S. PATENT DOCUMENTS

| | | | |
|---|---|---|---|
| 2,802,777 | 8/1957 | Lohr | 260/326.5 FN |
| 2,939,869 | 6/1960 | Carlson | 260/326.5 FN |
| 2,944,944 | 7/1960 | Clayton | 260/326.5 FN |
| 3,006,817 | 10/1961 | Ney | 260/326.5 FN |
| 3,186,984 | 6/1965 | Coltar | 260/326.5 FN |
| 3,644,402 | 2/1972 | Takagi et al. | 260/326.5 FN |
| 4,014,900 | 3/1977 | Pusztaszevi | 260/326.5 FN |
| 4,145,519 | 3/1979 | Bacskai | 260/326.5 FN |
| 4,216,151 | 8/1980 | Goetsch et al. | 260/326.5 FN |
| 4,264,501 | 4/1981 | Bour et al. | 260/326.5 FN |

FOREIGN PATENT DOCUMENTS

| | | | |
|---|---|---|---|
| 1295556 | 5/1969 | Fed. Rep. of Germany | 548/535 |
| 37-16038 | 10/1962 | Japan | 548/535 |

*Primary Examiner*—Donald G. Daus
*Assistant Examiner*—D. Springer

[57]  ABSTRACT

In a distillation process 2-pyrrolidones obtained from succinonitrile are purified by treating the impure liquid pyrrolidone with a strong base, fractionally distilling this product to yield, as distillate, polymerization grade purified 2-pyrrolidone, mixing the 2-pyrrolidone-containing residue from the fractional distillation with water and an acid, and extracting purified 2-pyrrolidone from the water/acid mixture. The latter purified 2-pyrrolidone products are suitable for recycling to the pyrrolidone synthesis or to make other products.

6 Claims, No Drawings

PROCESS FOR THE PURIFICATION OF 2-PYRROLIDONE

BACKGROUND AND SUMMARY OF THE INVENTION

The invention relates to a process for suitably purifying 2-pyrrolidones for subsequent polymerization to polypyrrolidone having a sufficiently high molecular weight.

Suitable methods for preparing 2-pyrrlidones by hydrogenating the corresponding succinonitriles followed by reacting water with the hydrogenation product are known, see for instance, U.S. Pat. Nos. 3,644,402; 4,123,438; and 4,193,925. According to these methods an aqueous pyrrolidone-containing solution is obtained from which fairly pure pyrrolidones can be recovered, for example, by fractional distillation. However, these recovered pyrrolidones do not satisfactorily polymerize to polypyrrolidones.

The many already proposed solutions for purifying the pyrrolidones have several drawbacks. Such drawbacks include, unacceptably high pyrrolidone losses, compatibility only with pyrrolidones produced from other than succinonitrile, or pyrrolidone products having a degree of purity unacceptably lower than that required for polymerizing pyrrolidones to polypyrrolidones.

Pyrrolidone can be purified in the liquid phase by dissolving therein a substantially water free solid hydroxide, such as KOH, and then subjecting the solution to a flash distillation using a molecular vacuum distillation apparatus having a heated flash vaporization surface, as described in U.S. Pat. No. 4,014,900. However, while that method achieves a pyrrolidone of a good degree of purity, the impurities and pyrrolidone losses amount to about 5% to 10% by weight of the starting material.

The process of the present invention provides a method for purifying 2-pyrrolidones obtained from the corresponding succinonitriles to yield a 2-pyrrolidone product of polymerization grade purity while minimizing the unrecoverable pyrrolidone losses.

DETAILED DESCRIPTION OF THE INVENTION

In the process according to the present invention, 2-pyrrolidones in the liquid phase are initially treated with a strong alkali or alkaline earth metal base, at an elevated temperature for a required period of time, and thereafter the resultant product is fractionally distilled to yield a purified polymerization-grade 2-pyrrolidone distillate. The pyrrolidone-containing distillation residue is subsequently treated by mixing it with water and acid, to liberate free pyrrolidone from the alkali or alkaline earth metal pyrrolidonate, which is then recovered by extraction with a water-immiscible organic solvent.

The distillation residue can thus be treated to yield 2-pyrrolidones which are suitable for subsequent conversion into various other products, for instance, N-vinyl pyrrolidone or N-methyl pyrrolidone. If desired, the 2-pyrrolidones from the residue can also be recirculated to the untreated aqueous reaction mixture for the preparation of pyrrolidone from succinonitrile, so that ultimately only pyrrolidones having polymerization grade purity are obtained.

The treatment of the pyrrolidone in the liquid phase with a strong base can be carried out at an elevated temperature of between about 80° C. and about 150° C. Temperatures between about 110° C. and about 130° C. are preferred. The duration of this treatment with a strong base may vary, for instance, between about 10 minutes and about 5 hours. A treatment duration exceeding 5 hours can also be employed but does not yield any additional advantage. Satisfactory results can generally be obtained with treatment durations of about 0.5 hours to about 3 hours. Suitable alkali or alkaline earth metal strong bases include, among others, potassium hydroxide, sodium hydroxide and barium hydroxide. Potassium hydroxide is preferred. Only relatively small amounts of the base are required, such as from about 0.2 grams to about 2 grams per 100 grams of pyrrolidone being purified. The amount of strong base required is dictated in part by the extent of the impurities present in the unpurified pyrrolidone. Usually an amount of strong base of about 0.5 grams to about 1.5 grams per 100 grams of pyrrolidone gives very satisfactory results.

The product obtained after treating the pyrrolidone with the strong base is then fractionally distilled, either at atmospheric pressure or by preference at a reduced pressure, of for instance from about 0.1 bar to about 0.3 bar.

The remaining fractional-distillation still-pot residue is mixed with water, for instance, about 20 grams to about 70 grams water per 100 grams of residue, and an acid. Suitable acids include, for instance, sulphuric acid, phosphoric acid, nitric acid and carbonic acid. Carbonic acid is preferred since a carbonate forms from the strong base remaining in the residue. The inorganic base can be recovered, if desired, from the carbonate in pure form via calcination. A sufficient amount of acid is used to completely convert the strong base remaining in the residue into a salt.

The extraction of the residue-containing aqueous mixture can be carried out counter-currently using various solvents, such as benzene, toluene and xylenes, at temperatures of about, for instance, 20° C. to about 50° C. About 1 gram to about 9 grams of extracting agent are required per gram of pyrrolidone to be extracted. The pyrrolidone recovery from the organic extraction phase can be, for instance, effected by evaporating the solvent or by crystallizing the pyrrolidone. If desired, the organic extraction phase can be subjected to a further water extraction. In that case an aqueous solution of pyrrolidone is located which can be recirculated to the aqueous reaction mixture being obtained in the preparation of pyrrolidone from succinonitrile.

The invention is illustrated in the following non-limiting example:

EXAMPLE

In the distillation flask of a vacuum distillation apparatus 1050 grams of pyrrolidone of 99% purity, obtained from succinonitrile as described in U.S. Pat. No. 4,123,438, is mixed with 8.76 grams KOH at approximately 45° C. Under a nitrogen atmosphere, the resultant mixture is then heated to 120° C. while reducing the pressure so far below 1 bar that the slight amount of water present in the potassium hydroxide and the impure pyrrolidone as well as 50 grams pyrrolidone distill over. The mixture is then maintained at 120° C. for one hour in the distillation flask at a higher pressure, but below 1 bar, without boiling. Then the pressure is reduced again until the mixture boils and the pyrrolidone distills over.

946.8 grams purified pyrrolidone is obtained. The pyrrolidone is colorless and does not discolor even when stored for one month in a brown bottle in a nitrogen atmosphere.

The distillation residue, 59.1 grams, is dissolved in 16.2 grams water and mixed with 60 grams toluene. While stirring, carbon dioxide is then passed through the mixture until the pH is approximately 13.2. The potassium pyrrolidonate remaining in the residue has then been converted into pyrrolidone and potassium carbonate. The supernatant toluene layer is separated off. The remaining mixture is then extracted four times, each time with 60 grams toluene. After evaporating the toluene from the combined toluene layers, 54 grams of 98.8% pure pyrrolidone is obtained which is suitable for conversion into, for instance, N-vinyl pyrrolidone. If desired, this pyrrolidone can be recirculated to the section where the reaction mixture obtained in the preparation of pyrrolidone from succinonitrile is worked up.

After the extraction with toluene, potassium hydroxide can be recovered in a known way from the contaminated potassium carbonate and water mixture remaining behind.

Polymerization and Determination of The Color of the Purified Pyrrolidone

In a nitrogen atmosphere, 120 ml of the thus-purified pyrrolidone is introduced into a 250 ml flask provided with a distillation column, and then heated to the boiling point under vacuum conditions. The temperature in the top of the distillation column then is about 96° C. and about 125° C. in the flask. Subsequently, solid potassium hydroxide (0.1 mole KOH per mole pyrrolidone in 100 ml pyrrolidone) is added in a nitrogen atmosphere. The water formed in the reaction is distilled off under vacuum conditions within a minute. In addition, 20 ml pyrrolidone are distilled off. The residue which remains is rapidly cooled to 40° C. in a nitrogen atmosphere.

Part of the residue is cooled further to 25° C. and subsequently the extinction at 390 nm of this part is measured in a glass cell. The color index number is 9° Hazen. For comparison purposes, if the purification according to the example is carried out without keeping the mixture at 120° C. for one hour before the distillation, all other conditions remaining unchanged, the color index number is 100° Hazen.

While under vacuum at 40° C., carbon dioxide is added to the said remaining residue portion, with 0.3 mole $CO_2$ per mole potassium pyrrolidonate present. This takes about 20 minutes. The resultant mixture is then maintained at approximately 50° C. for 24 hours under a nitrogen atmosphere. The white polymer thereby produced is then ground, washed and dried.

The polymerization conversion is about 50%. The relative viscosity, at 1 gram polypyrrolidone per 100 grams $H_2SO_4$, is 46 which corresponds to a molar weight of 410,000.

What is claimed is:

1. In a fractional-distillation process for purifying impure 2-pyrrolidone obtained from succinonitrile comprising the combination of steps of:
    (a) first heating impure pyrrolidone in the liquid state for about 0.5 hour to about 3 hours at about 80° C. to about 150° C. in the presence of a substantially water-free strong inorganic alkali or alkaline earth metal base, wherein about 0.5 gram to about 1.5 grams of said strong base is used per 100 grams of impure pyrrolidone;
    (b) thereafter fractionally distilling the mixture obtained in step (a) to obtain a polymerization-grade purified pyrrolidone distillate, while leaving a metal pyrrolidonate-containing residue;
    (c) mixing said metal pyrrolidonate-containing residue with water and an inorganic acid to liberate free pyrrolidone wherein said inorganic acid is selected from the group consisting of sulphuric acid, phosphoric acid, nitric acid or carbonic acid; and
    (d) extracting high purity pyrrolidone from the mixture obtained in step (c) with a water-immiscible organic solvent.

2. Process according to claim 1, wherein said temperature is from 110° C. to about 130° C.

3. Process according to claim 1 wherein sodium hydroxide, barium hydroxide or potassium hydroxide is used as said strong base.

4. Process according to claim 1, wherein said fractional distillation is carried out at a pressure of about 0.1 bar to about 0.3 bar.

5. Process according to claim 1, wherein said acid of step (c) is carbonic acid.

6. A fractional-distillation process for purifying an impure 2-pyrrolidone obtained from succinonitule comprising the combination of steps of:
    (a) a fractionally distilling off polymerization grade pyrrolidone as a distillate from a mixture obtained by heating for about 0.5 hour to about 3 hours at about 80° C. to about 150° C. impure pyrrolidone in the liquid state in the presence of about 0.5 gram to about 1.5 grams of substantially water-free strong inorganic alkali or alkaline earth metal base wherein said base is selected from the group consisting of sodium hydroxide, barium hydroxide, or potassium hydroxide thereby leaving a residue containing metal pyrrolidonate;
    (b) mixing the residue containing metal pyrrolidonate with water and introducing $CO_2$ into said residue thereby liberating free pyrrolidone;
    (c) extracting a high purity pyrrolidone product from the said residue-mixture obtained in step (b) with a water-immiscible organic solvent.

* * * * *